United States Patent [19]

Weller, III et al.

[11] Patent Number: 4,740,508

[45] Date of Patent: Apr. 26, 1988

[54] UREIDOALKANOYLAMINOCARBONYL AMINO AND IMINO ACIDS AND ESTERS

[75] Inventors: Harold N. Weller, III; Eric M. Gordon, both of Pennington, N.J.

[73] Assignee: E. R. Squibb & Sons, Inc., Princeton, N.J.

[21] Appl. No.: 726,264

[22] Filed: Apr. 22, 1985

[51] Int. Cl.⁴ .................. C07D 401/00; C07D 211/06; C07D 211/60; A61K 31/44
[52] U.S. Cl. .................... 514/255; 514/326; 514/330; 514/422; 514/423; 544/300; 546/206; 546/227; 546/238; 546/256; 548/523; 548/527; 548/530; 548/532; 548/535; 564/153; 564/168; 564/185
[58] Field of Search ............... 546/208, 227, 238, 256; 560/169, 170; 548/532, 535, 523, 530, 527; 564/168, 153, 185; 544/360; 514/255, 326, 330, 422, 423

[56] References Cited

U.S. PATENT DOCUMENTS

| | | | |
|---|---|---|---|
| 4,329,473 | 5/1982 | Almquist et al. | 546/281 |
| 4,621,092 | 11/1986 | Natarajan et al. | 514/343 |
| 4,623,729 | 11/1986 | Natarajan et al. | 546/256 |

FOREIGN PATENT DOCUMENTS 17203  1/1984  Australia ........................... 546/208

OTHER PUBLICATIONS

Meyer et al., "Novel Synthesis of . . . ", J. Med. Chem., 1981, vol. 24, pp. 964–969.
Almquist et al., "Derivatives of Potent Angiotensin Converting Enzyme Inhibitor . . . ", J. Med. Chem., 1982, vol. 25, 1292–1299.

Primary Examiner—Richard L. Raymond
Assistant Examiner—Covington, Raymond
Attorney, Agent, or Firm—Lawrence S. Levinson; Stephen B. Davis

[57]  ABSTRACT

Compounds of the formula

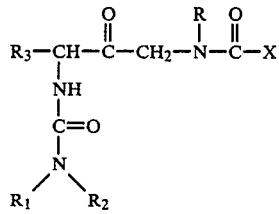

are disclosed. These compounds are useful as hypotensive agents due to their angiotensin converting enzyme inhibition activity and depending upon the definition of X may also be useful as analgesics due to their enkephalinase inhibition activity.

8 Claims, No Drawings

UREIDOALKANOYLAMINOCARBONYL AMINO AND IMINO ACIDS AND ESTERS

BACKGROUND OF THE INVENTION

Natarajan et al. in Australian Patent Application No. 17,203 disclose acylalkylaminocarbonyl substituted amino and imino acid compounds of the formula

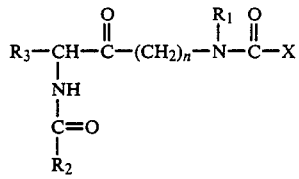

wherein $R_2$ is certain aryl, aralkyl, heterocyclo, or alkylene-heterocyclo groups. These compounds possess angiotensin converting enzyme inhibition activity and enkephalinase inhibition activity depending upon the definition of X.

Almquist et al. in U.S. Pat. No. 4,329,473 disclose angiotensin converting enzyme inhibiting compounds of the formula

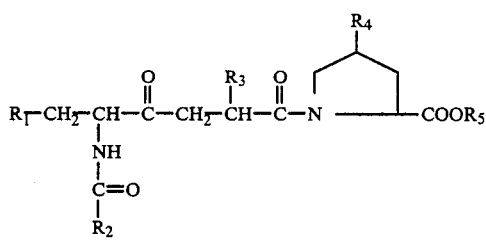

wherein $R_2$ is aryl, alkyl, alkoxy or benzyloxy.

SUMMARY OF THE INVENTION

This invention is directed to novel compounds of the formula

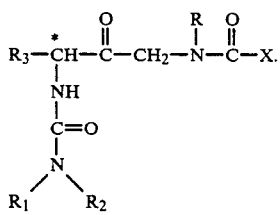  (I)

R is hydrogen, lower alkyl, halo substituted lower alkyl, —$(CH_2)_m$—cycloalkyl,

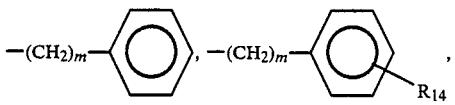

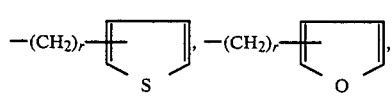

-continued

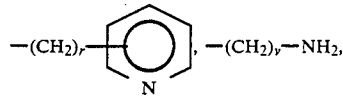

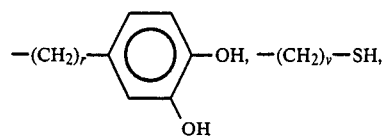

—$(CH_2)_v$—OH, —$(CH_2)_r$—S—lower alkyl,

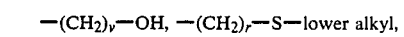

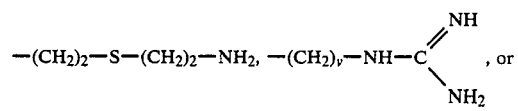

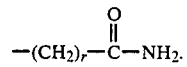

v is an integer from 2 to 6.

$R_1$ and $R_2$ are independently selected from hydrogen, lower alkyl, halo substituted lower alkyl, —$(CH_2)_m$—cycloalkyl,

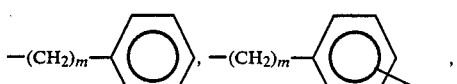

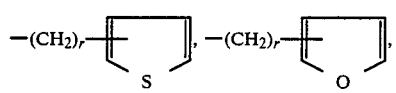

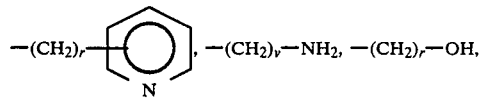

—$(CH_2)_r$—O—lower alkyl, —$(CH_2)_v$—NH—C(=O)—lower alkyl,

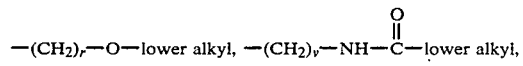

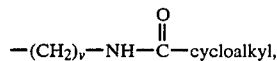

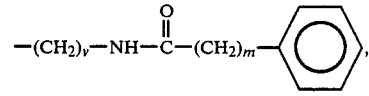

or $R_1$ and $R_2$ taken with the N atom form a heterocyclo ring of the formula

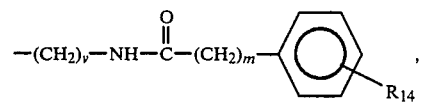

-continued
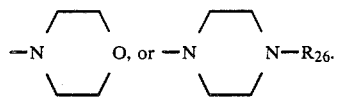
R$_{26}$ is hydrogen or lower alkyl.
X is an amino or imino acid or ester of the formula
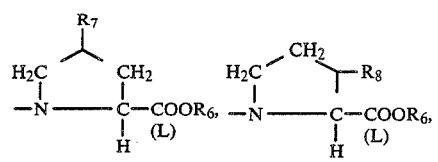
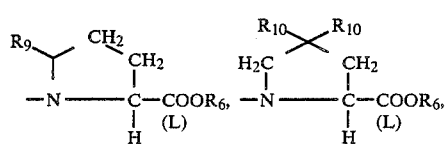
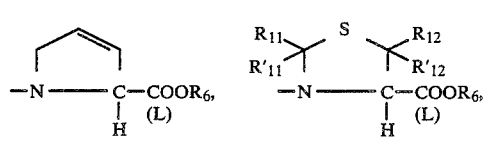
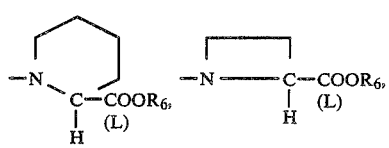
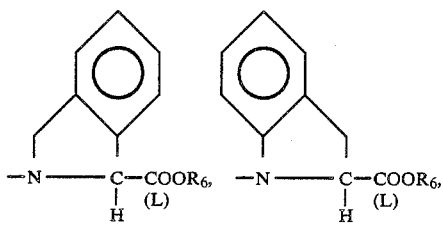
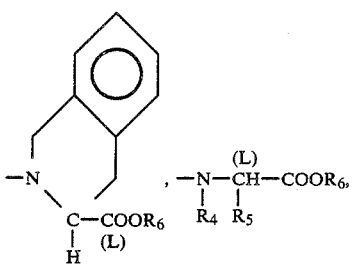
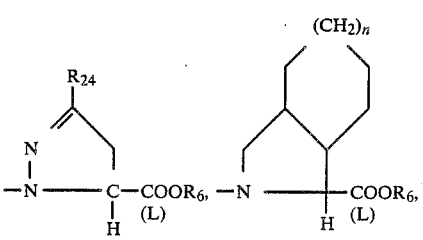
-continued
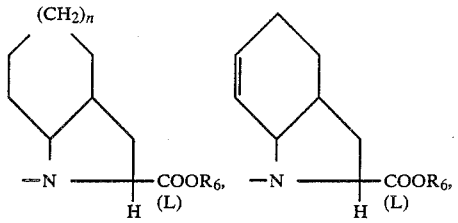
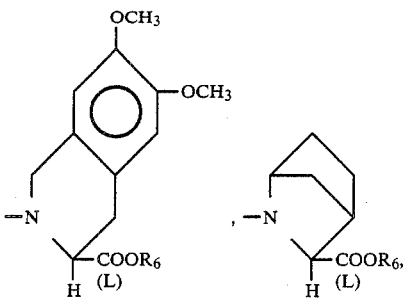
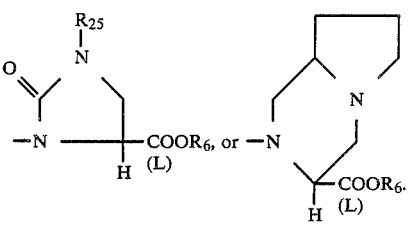
n is zero, one or two.
R$_{25}$ is lower alkyl of 1 to 4 carbons or
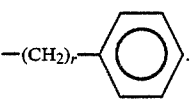
R$_7$ is hydrogen, lower alkyl, halogen, hydroxy,
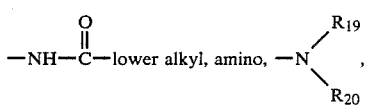
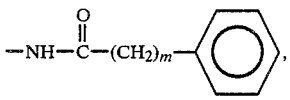
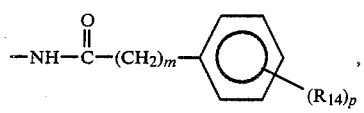
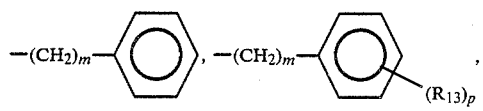
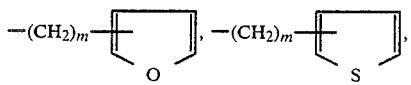

-continued

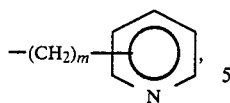, a 1- or 2-naphthyl of the formula

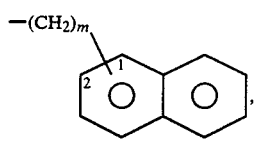, a substituted 1- or 2-naphthyl of the formula

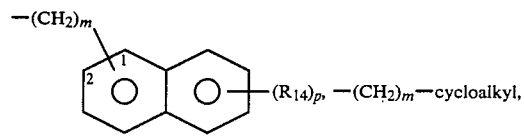, $-(CH_2)_m-$cycloalkyl,

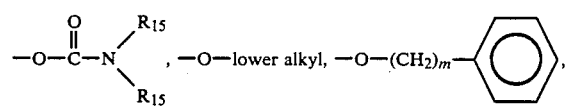,

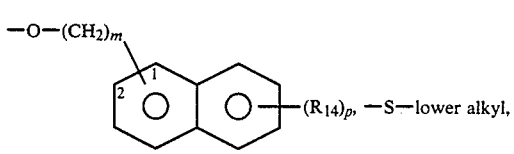

a 1- or 2-naphthyloxy of the formula

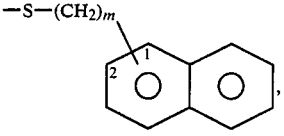, a substituted 1- or 2-naphthyloxy of the formula

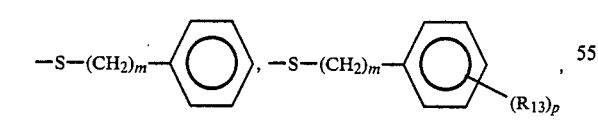

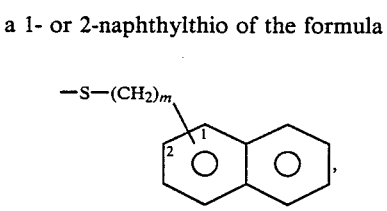

a 1- or 2-naphthylthio of the formula

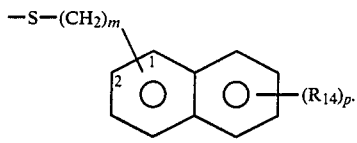

$R_8$ is halogen,

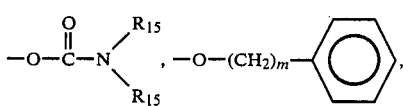,

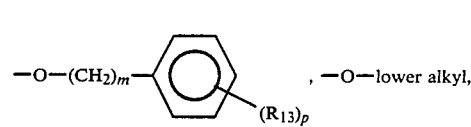, $-O$—lower alkyl, a 1- or 2-naphthyloxy of the formula

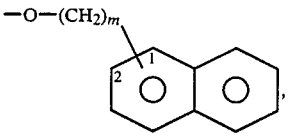, a substituted 1- or 2-naphthyloxy of the formula

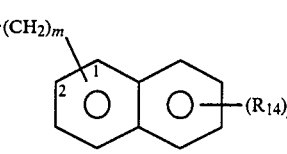, $-S$—lower alkyl,

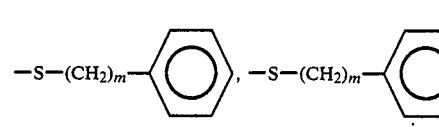, a 1- or 2-naphthylthio of the formula

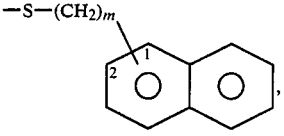, or a substituted 1- or 2-naphthylthio of the formula

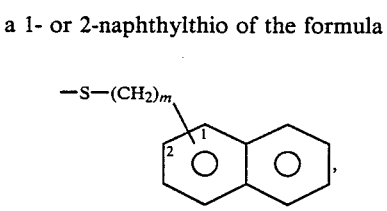

$R_9$ is keto,

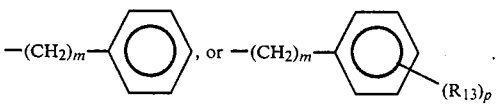

or a substituted 1- or 2-naphthylthio of the formula $R_{10}$ is halogen or $-Y-R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

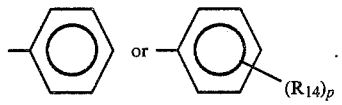

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two, three, or four.

p is one, two or three provided that p is more than one only if $R_{13}$ or $R_{14}$ is methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

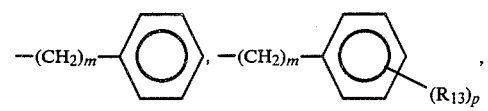

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl,

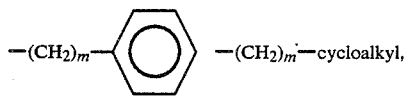

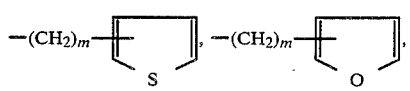

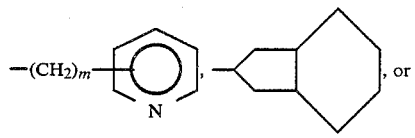

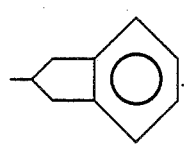

$R_5$ is hydrogen, lower alkyl,

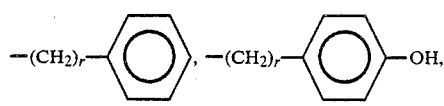

-continued

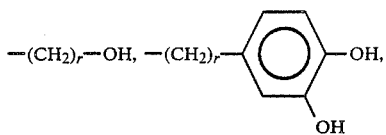

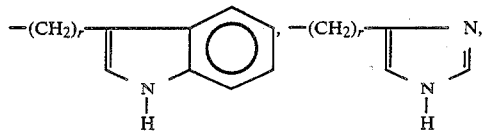

$-(CH_2)_r-NH_2$, $-(CH_2)_r-SH$, $-(CH_2)_r-S-$lower alkyl,

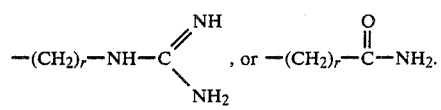

r is an integer form 1 to 4

$R_{19}$ is lower alkyl, benzyl or phenethyl.

$R_{20}$ is hydrogen, lower alkyl, benzyl or phenethyl.

$R_3$ is hydrogen, lower alkyl,

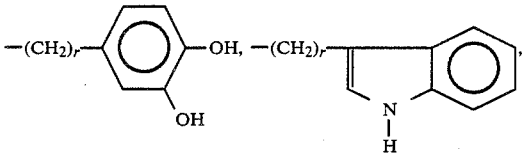

halo substituted lower alkyl, $-(CH_2)_m-$cycloalkyl,

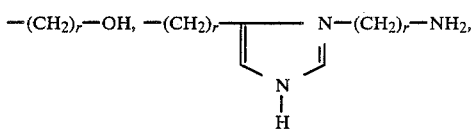

$-(CH_2)_r-OH$, $-(CH_2)_r-$

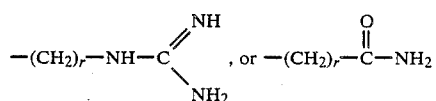

$-(CH_2)_r-SH$, $-(CH_2)_r-S-$lower alkyl, $-(CH_2)_r-NH-\underset{NH_2}{\overset{NH}{C}}$, or $-(CH_2)_r-\overset{O}{\overset{\|}{C}}-NH_2$ wherein m, $R_{14}$, p and r are as defined above.

$R_6$ is hydrogen, lower alkyl, benzyl, benzhydryl,

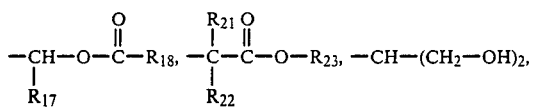

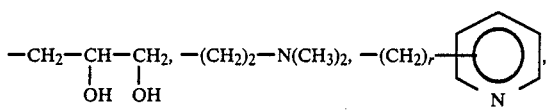

or a salt forming ion.

R$_{17}$ is hydrogen, lower alkyl, cycloalkyl, or phenyl.
R$_{18}$ is hydrogen, lower alkyl, lower alkoxy or phenyl.
R$_{21}$ and R$_{22}$ are independently selected from hydrogen and lower alkyl.
R$_{23}$ is lower alkyl.
R$_{24}$ is hydrogen, lower alkyl,

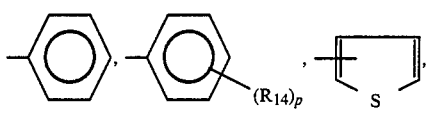

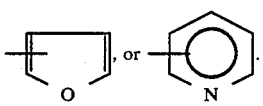

DETAILED DESCRIPTION OF THE INVENTION

This invention in its broadest aspects relates to the amino and imino acid and ester compounds of formula I and to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro. The term halo substituted lower alkyl refers to such alkyl groups in which one or more carbons have been replaced by a halogen, i.e., CF$_3$, CH$_2$Cl$_3$, CH$_2$Br, etc.

The symbols

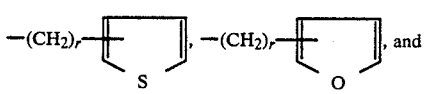

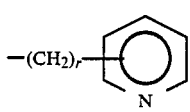

represent that the alkylene bridge is attached to an available carbon atom.

The compounds of formula I are obtained by treating an amine of the formula

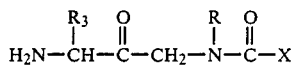

particularly the hydrochloride salt thereof, wherein R$_6$ in the definition of X is an easily removable protecting group such as benzyl, benzhydryl, t-butyl, etc., with p-nitrophenyl chloroformate or phosgene in the presence of N-methylmorpholine followed by treatment with an amine of the formula

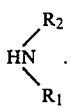

Alternatively, the amine of formula III could first be treated with p-nitrophenyl chloroformate or phosgene and the resultant product then treated with the amino intermediate of formula II.

The compounds of formula I wherein R$_1$ and R$_2$ are both hydrogen can be prepared by employing ammonia as the reagent of formula III in the first procedure described above.

Removal of the R$_6$ protecting group, for example by hydrogenation when R$_6$ is benzyl, yields the acid products of formula I, i.e., R$_6$ is hydrogen.

The amino intermediate of formula II can be prepared as follows. An amino acid derivative of the formula

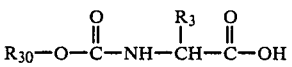

wherein R$_{30}$ is t-butyl, —CH$_2$—CCl$_3$, benzhydryl,

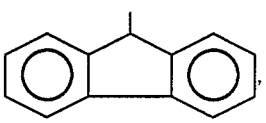

or —(CH$_2$)$_2$—Si(CH$_3$)$_3$ is treated sequentially with isobutylchloroformate and a tertiary base such as N-methylmorpholine followed by reaction with diazomethane and treatment with hydrogen chloride to give

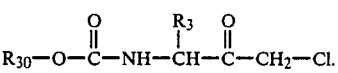

The chloride of formula V is treated with a substituted benzylamine of the formula

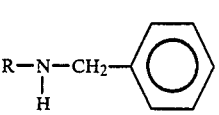

to give

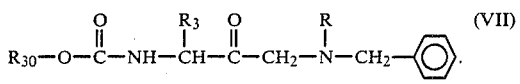 (VII)

Removal of the benzyl protecting group, for example, by hydrogenation gives

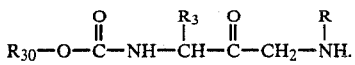 (VIII)

The amine of formula VIII, particularly the p-toluenesulfonic acid salt thereof, is treated with the chlorocarbonylamine of the formula

 (IX)

in the presence of a base such as triethylamine, wherein $R_6$ in the definition of X is an easily removable protecting group, followed by removal of the t-butyl, benzyhydryl, $-CH_2-CCl_3$, $-(CH_2)_2-Si(CH_3)_3$, or

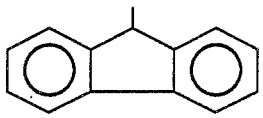

$R_{30}$ group, for example by treating with hydrogen chloride when $R_{30}$ is t-butyl, to yield the amino intermediate of formula II.

In the above reactions, if R is hydrogen then the N-atom is protected, for example by a t-butoxycarbonyl group which can be removed by hydrogenation following completion of the reaction. Also, if $R_{26}$ is hydrogen then that N-atom is protected, for example, by a benzyloxycarbonyl group which can be removed following completion of the reaction. Similarly, if any or all of R, $R_1$, $R_2$, $R_3$ and $R_5$ are

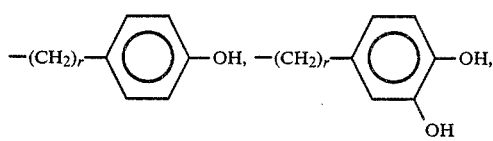

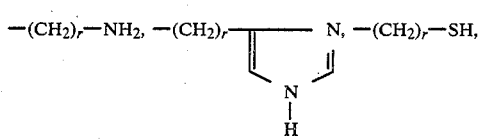

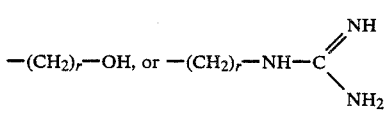

then the hydroxyl, amino, imidazolyl, mercaptan or guanidinyl function should be protected during the reaction. Suitable protecting groups include benzyloxycarbonyl, t-butoxycarbonyl, benzyl, trimethylsilylethylcarbonyl, benzhydryl, trityl, etc., and nitro in the case of guanidinyl. The protecting group is removed by hydrogenation, treatment with acid, or other known methods following completion of the reaction.

The ester products of formula I wherein $R_6$ is

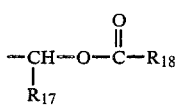

may be obtained by employing the amino or imino acid ester of formula III in the above reactions with such ester group already in place.

The ester products of formula I wherein $R_6$ is

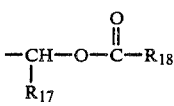

can also be obtained by treating the product of formula I wherein $R_6$ is hydrogen with a molar excess of the compound of the formula

 (X)

wherein L is a leaving group such as chlorine, bromine, tolylsulfonyl, etc.

The ester products of formula I wherein $R_6$ is

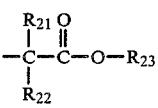

can be prepared by treating the product of formula I wherein $R_6$ is hydrogen with a molar excess of the compound of the formula

 (XI)

The ester products of formula I wherein $R_6$ is $-CH-(CH_2-OH)_2$ or $-CH_2-CH-CH_2$
                              $\,\,\,\,\,\,\,\,\,\,\,\,\,\,\,\,\,\,\,\,\,\,\,\,\,\,\,$  |   |
                              $\,\,\,\,\,\,\,\,\,\,\,\,\,\,\,\,\,\,\,\,\,\,\,\,\,\,\,$  OH  OH can be prepared by coupling the product of formula I wherein $R_6$ is hydrogen with a molar excess of the compound of the formula

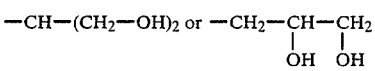 (XII)

or the formula

 (XIII)

in the presence of a coupling agent such as dicyclohexylcarbodiimide and the optional presence of a catalyst such as dimethylaminopyridine followed by removal of the hydroxyl protecting group.

Similarly, the ester products of formula I wherein $R_6$ is

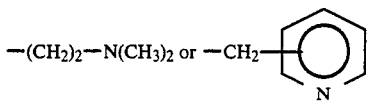

can be prepared by coupling the product of formula I wherein $R_6$ is hydrogen with a molar excess of the compound of formula

  (XIV)

or the formula

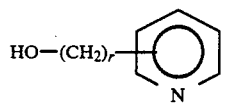  (XV)

in the presence of a coupling agent such as dicylohexylcarbodiimide and the optional presence of a catalyst such as dimethylaminopyridine.

The products of formula I wherein $R_7$ is amino may be obtained by reducing the corresponding products of formula I wherein $R_7$ is azido.

Preferred compounds of this invention are those of formula I wherein:

X is

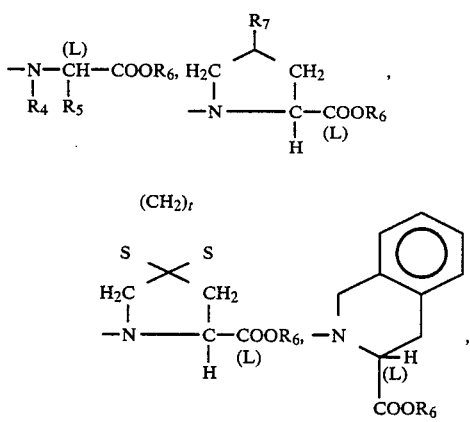

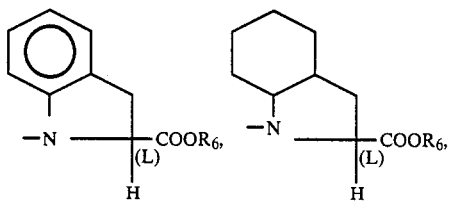

-continued

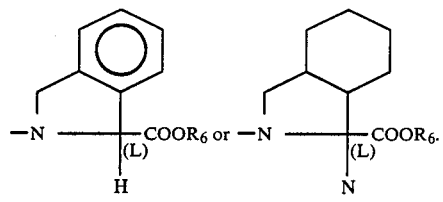

$R_6$ is hydrogen, straight or branched chain lower alkyl of 1 to 4 carbons, or an alkali metal salt ion.

$R_4$ is cyclohexyl or phenyl and $R_5$ is hydrogen.

$R_4$ is hydrogen and $R_5$ is methyl,

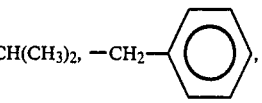

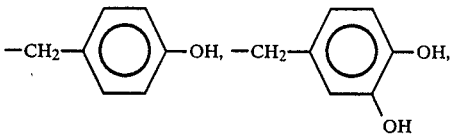

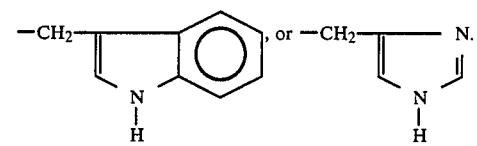

$R_7$ is hydrogen, cyclohexyl, lower alkoxy of 1 to 4 carbons,

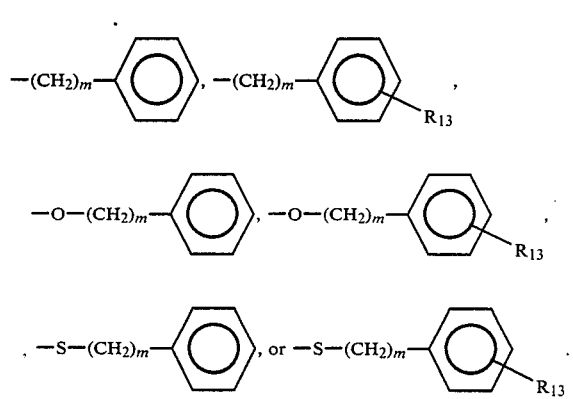

$R_{13}$ is methyl, methoxy, methylthio, Cl, Br, F, or hydroxy.

m is zero, one or two.

t is two or three.

R is straight or branched chain lower alkyl of 1 to 4 carbons.

$R_1$ and $R_2$ are independently selected from straight or branched chain lower alkyl of 1 to 4 carbons or $R_1$ is cyclohexyl and $R_2$ is hydrogen or $R_1$ and $R_2$ taken together with the N atom to which they are attached complete a heterocyclo ring of the formula

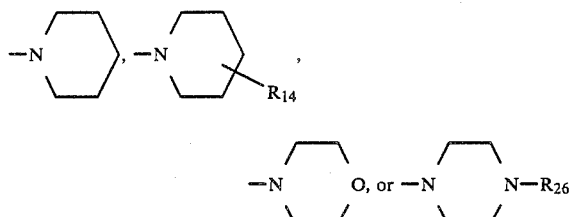

wherein $R_{26}$ is hydrogen or straight or branched chain lower alkyl of 1 to 4 carbons.

$R_3$ is straight or branched chain lower alkyl of 1 to 4 carbons,

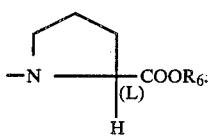

$R_{14}$ is methyl, methoxy, methylthio, Cl, Br, F, or hydroxy.

Most preferred compounds of this invention are those of formula I wherein:

X is

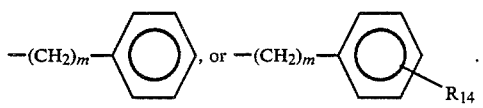

R is methyl.

$R_6$ is hydrogen or an alkali metal salt ion.

$R_1$ and $R_2$ are each methyl or $R_1$ is cyclohexyl and $R_2$ is hydrogen or $R_1$ and $R_2$ taken together with the N atom to which they are attached complete a heterocyclo ring of the formula

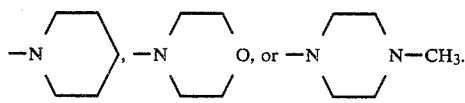

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The compounds of formula I when $R_3$ is other than hydrogen contain an asymmetric center as represented by the * in formula I. Thus, the compounds of formula I can exist in diasteromeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

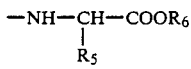

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[[Methyl[(S)-2-oxo-4-phenyl-3-[(1-piperidinylcarbonyl)amino]butyl]amino]carbonyl]-L-proline (a)

(S)-[3-Chloro-2-oxo-1-(phenylmethyl)propyl]carbamic acid, 1,1-dimethylethyl ester To a stirred solution of N-[(1,1-dimethylethoxy)carbonyl]-L-phenylalanine (26.5 g., 100 mmole) in tetrahydrofuran (150 ml.) at −20° is added isobutylchloroformate (13 ml., 100 mmole). N-Methylmorpholine (11 ml., 100 mmole) is then added in drops. The solution is stirred between −15° C. and −20° C. for fifteen minutes and then filtered. Tetrahydrofuran (25 ml.) is used for the washings. The filtrate is added to a cold (ice bath) ethereal solution of diazomethane in drops. After the addition is over, the ice bath is removed, and the reaction mixture is stirred at ambient temperature for 2 hours. Nitrogen is blown over the solution and the volume is reduced to 400 ml. The reaction mixture is then stirred in an ice bath and hydrogen chloride in acetic acid (2N, 55 ml.) is added in drops. After the addition is over, the ice bath is removed and the reaction mixture is stirred for 15 minutes at room temperature. The reaction mixture is evaporated in vacuo and the residue on attempted dissolution in ether affords 6.2 g. of (S)-[3-chloro-2-oxo-1-(phenylmethyl)propyl]carbamic acid, 1,1-dimethylethyl ester; m.p. 104°–105°; $[\alpha]_D^{22} = +20.3°$ (c=2, chloroform). The mother liquor on concentration and after crystallization from ether/hexane gives an additional 17.65 g. of product.

(b)

(S)-[3-[Methyl(phenylmethyl)amino]-2-oxo-1-(phenylmethyl)propyl]carbamic acid, 1,1-dimethylethyl ester, p-toluenesulfonate salt A solution of (S)-[3-chloro-2-oxo-1-(phenylmethyl)propyl]carbamic acid, 1,1-dimethylethyl ester (6.43 g., 21.6 mmole), sodium bicarbonate (2.17 g., 25.9 mmole), sodium iodide (1.62 g., 11.0 mmole) and benzylmethylamine (2.76 ml., 2.14 mmole) in dimethylformamide (60 ml.) is stirred at room temperature for 4 hours. The resulting solution is concentrated and partitioned between ether and water. The ether layer is washed with water (twice) and extracted with 1N hydrochloric acid (five times). The combined extracts are made basic using sodium bicarbonate and extracted with ethyl acetate. The ethyl acetate extracts are dried (MgSO4) and concentrated. The crude crystalline residue is dissolved in ether and a solution of p-toluenesulfonic acid (3.0 g., 28 mmole) in ethyl acetate is added. The resulting pink crystals are triturated with hot ethyl acetate and collected to give 6.5 g. of (S)-[3-[methyl(phenylmethyl)amino]-2-oxo-1-(phenylmethyl)propyl]carbamic acid, 1,1-dimethylethyl ester, p-toluenesulfonate salt as a white solid; m.p. 150°–152°.

(c)

(S)-[3-(Methylamino)-2-oxo-1-(phenylmethyl)propyl]carbamic acid, 1,1-dimethylethyl ester, hydrochloride salt A mixture of the p-toluenesulfonate salt product from part (b) (6.5 g., 11.7 mmole) and palladium hydroxide (20%) in methanol is hydrogenated at atmospheric pressure and room temperature for 1.5 hours. The resulting solution is filtered, concentrated, and triturated with ether to give 4.75 g. of a white crystalline solid. A portion of this material is partitioned between ethyl acetate and 10% sodium bicarbonate. The organic layer is treated with hydrochloric acid/ether to give the crude hydrochloric salt as blue-green solid. Recrystallization from methanol/ether gives (S)-[3-(methylamino)-2-oxo-1-(phenylmethyl)propyl]carbamic acid, 1,1-dimethylethyl ester, hydrochloride salt; m.p. 164°–169°.

(d)

1-[[[(S)-3-[[(1,1-Dimethylethoxy)carbonyl]amino]-2-oxo-4-phenylbutyl]methylamino]carbonyl]-L-proline, phenylmethyl ester N-Methylmorpholine (0.46 ml., 4.2 mmole) is added to a stirring suspension of L-proline, phenylmethyl ester, hydrochloride salt (0.39 g., 1.6 mmole) in methylene chloride (dry, distilled) at −40° followed by phosgene in benzene (approximately 1M, 2.5 ml., 2.5 mmole). The mixture is stirred at −30° for one hour. The ice bath is removed and the mixture is stirred for an additional hour. The mixture is then concentrated in vacuo and diluted with methylene chloride. (S)-[3-(Methylamino)-2-oxo-1-(phenylmethyl)propyl]carbamic acid, 1,1-dimethylethyl ester, hydrochloride salt (0.34 g., 1.0 mmole) is added to the solution and the mixture is stirred overnight. The resulting solution is diluted with methylene chloride and washed with 1N hydrochloric acid and 10% sodium bicarbonate, dried (MgSO4) and concentrated. The crude product (0.61 g.) is combined with material from a previous run (0.56 g.) and chromatographed on LPS-1 silica gel using hexane:ethyl acetate (2:1) as the eluant. The combined fractions are rechromatographed on LPS-1 using ether:ethyl acetate (10:1) as eluent. Fractions containing the desired product ($R_f = 0.43$, hexane:ethyl acetate, 1:1) are combined and concentrated to give 0.26 g. of 1-[[[(S)-3-[[(1,1-dimethylethoxy)carbonyl]amino]-2-oxo-4-phenylbutyl]methylamino]carbonyl]-L-proline, phenylmethyl ester.

(e)

1-[[[(S)-3-Amino-2-oxo-4-phenylbutyl]methylamino]carbonyl]-L-proline, phenylmethyl ester A solution of 1-[[[(S)-3-[[(1,1-dimethylethoxy)carbonyl]amino]-2-oxo-4-phenylbutyl]methylamino]carbonyl]-L-proline, phenylmethyl ester (7.12 g., 13.6 mmole) is stirred in a saturated solution of hydrochloric acid/ethyl acetate for one hour. The resulting precipitate is collected and washed with ethyl acetate to give 5.63 g of 1-[[[(S)-3-amino-2-oxo-4-phenylbutyl]methylamino]carbonyl]-L-proline, phenylmethyl ester; m.p. 174°–175°; $[\alpha]_D^{25} = +16.20°$. TLC (silica gel; chloroform:methanol:acetic acid, 4:1:1) $R_f=0.60$.

(f)

1-[[[(S)-3-[[(4-Nitrophenoxy)carbonyl]amino]-2-oxo-4-phenylbutyl]methylamino]carbonyl]-L-proline, phenylmethyl ester N-Methylmorpholine (2.0 ml., 18.0 mmole) is added over a period of 5 minutes to a cooled (−30°) mixture of 1-[[[(S)-3-amino-2-oxo-4-phenylbutyl]methylamino]carbonyl]-L-proline, phenylmethyl ester (3.6 g., 8.0 mmole) and p-nitrophenyl chloroformate (1.6 g., 8.0 mmole) in methylene chloride (30 ml.). The resulting mixture is stirred for 15 more minutes in the cold bath and 20 minutes after removal of the bath. The mixture is washed with water (2×), 1N hydrochloric acid, 10% sodium bicarbonate (4×), and 1N hydrochloric acid. The organic layer is dried (MgSO4) and concentrated to a red oil. The crude material is filtered through silica gel using chloroform and chloroform:ethyl acetate (1:1) as eluants. Fractions containing the desired product ($R_f=0.57$, ethyl acetate) are combined and concentrated. The residue is dissolved in methanol and cooled. Crystals are filtered off and the filtrate is concentrated to give 2.95 g. of 1-[[[(S)-3-[[(4-nitrophenoxy)carbonyl]amino]-2-oxo-4-phenylbutyl]methylamino]carbonyl]-L-proline, phenylmethyl ester as a yellow oil.

(g)

1-[[Methyl[(S)-2-oxo-4-phenyl-3-[(1-piperidinylcarbonyl)amino]butyl]amino]carbonyl]-L-proline, phenylmethyl ester A solution of piperidine (0.5 ml., 5.2 mmole) in toluene (15 ml.) is added dropwise over five minutes to a cooled solution (0°) of 1-[[[(S)-3-[[(4-nitrophenoxy)carbonyl]amino]-2-oxo-4-phenylbutyl]methylamino]carbonyl]-L-proline, phenylmethyl ester (1.48 g., 2.6 mmole) in toluene (40 ml.) in an ice bath. The solution is immediately turns yellow. The resulting solution is stirred at room temperature for 30 minutes, diluted with water and washed sequentially with 1N hydrochloric acid, 10% sodium bicarbonate, and water. The organic layer is dried (MgSO4) and concentrated. The residue (1.5 g.) is chromatographed on LPS-1 silica gel using an elution gradient of 50→100% ethyl acetate in hexane. Fractions containing the desired product ($R_f=0.54$ traces at $R_f=0.4, 0.6$, ethyl acetate) are combined and concentrated to a yellow oil (0.85 g.). The residue is then purified by preparative layer chromatography using ethyl acetate as eluant to give 0.81 g. of 1-[[methyl[(S)-2-oxo-4-phenyl-3-[(1-piperidinylcarbonyl)amino]butyl]amino]carbonyl]-L-proline, phenylmethyl ester as a pale yellow oil.

(h)

1-[[Methyl[(S)-2-oxo-4-phenyl-3-[(1-piperidinylcarbonyl)amino]butyl]amino]carbonyl]-L-proline A suspension of the phenylmethyl ester product from part (g) (0.8 g., 1.5 mmole) in methanol and palladium hydroxide (20% on carbon) is hydrogenated at room temperature and atmospheric pressure for 30 minutes. The mixture is filtered, the solids are rinsed with methanol, and the filtrate is concentrated to give 0.42 g. of yellow oil. The residue is chromatographed on LPS-1 silica gel using an elution gradient of 3→10% acetic acid in chloroform. Fractions containing the desired material are combined and concentrated. The residue is dissolved in methanol/water, filtered, concentrated (methanol removed) and lyophilized to give a white solid. The material is rechromatographed on CC-4 silica gel using ethyl acetate as the eluant. Fractions containing the desired produced are combined and lyophilized from water/dioxane to give 1-[[methyl[(S)-2-oxo-4-phenyl-3-[(1-piperidinylcarbonyl)amino]butyl]amino]carbonyl]-L-proline as a white solid; m.p. 69°–72°; $[\alpha]_D^{25} = -37°$ (c=0.2, methanol). TLC (silica gel; toluene:acetic acid, 4:1) $R_f=0.18$.

Anal. calc'd. for $C_{23}H_{32}N_4O_5 \cdot 1H_2O$: C, 59.72; H, 7.41; N, 12.11. Found: C, 59.86; H, 7.07; N, 11.67.

EXAMPLE 2

1-[[Methyl[(S)-3-[(4-morpholinylcarbonyl)amino]-2-oxo-4-phenylbutyl]amino]carbonyl]-L-proline (a)

1-[[Methyl[(S)-3-[(4-morpholinylcarbonyl)amino]-2-oxo-4-phenylbutyl]amino]carbonyl]-L-proline, phenylmethyl ester Morpholine (1 ml., 11.4 mmole) is added to a stirring solution of 1-[[[(S)-3-[[(4-nitrophenoxy)carbonyl]amino]-2-oxo-4-phenylbutyl]methylamino]carbonyl]-L-proline, phenylmethyl ester (0.9 g., 1.58 mmole) in toluene at 0° in one portion. The reaction mixture turns yellow in 15 minutes and TLC indicates complete loss of starting material after 30 minutes. The resulting solution is washed sequentially with water, 1N hydrochloric acid, and 10% sodium bicarbonate. The organic layer is dried (MgSO4) and concentrated. The crude product is purified by preparative layer chromatography to give 0.26 g. of 1-[[methyl[(S)-3-[(4-morpholinylcarbonyl)amino]carbonyl]-2-oxo-4-phenylbutyl]amino]carbonyl]-L-proline, phenylmethyl ester as a yellow oil. TLC (ethyl acetate) $R_f=0.18$.

(b)

1-[[Methyl[(S)-3-[(4-morpholinylcarbonyl)amino]-2-oxo-4-phenylbutyl]amino]carbonyl]-L-proline A solution of the phenylmethyl ester product from part (a) (0.26 g., 0.48 mmole) in methanol containing palladium hydroxide on carbon is hydrogenated at room temperature and atmospheric pressure for 30 minutes. The mixture is filtered (Celite), the solids rinsed with methanol, and the filtrate is concentrated. The residue is triturated with ether and dried under vacuum to give 0.16 g. of 1-[[methyl[(S)-3-[(4-morpholinylcarbonyl)amino]-2-oxo-4-phenylbutyl]amino]carbonyl]-L-proline as a white solid; m.p. 75°–90°; $[\alpha]_D = -38°$ (c=0.9, methanol). TLC(silica gel; chloroform:methanol:acetic acid, 4:1:1) $R_f=0.8$, trace at $R_f=0.2$.

Anal. calc'd. for $C_{22}H_{30}N_4O_6 \cdot 0.71H_2O$: C, 57.54; H, 6.89; N, 12.20. Found: C, 57.54; H, 6.78; N, 11.97.

EXAMPLE 3

1-[[[(S)-3-[[(Cyclohexylamino)carbonyl]amino]-2-oxo-4-phenylbutyl]methylamino]carbonyl]-L-proline (a)

1-[[[(S)-3-[[(Cyclohexylamino)carbonyl]amino]-2-oxo-4-phenylbutyl]methylamino]carbonyl-L-proline, phenylmethyl ester Cyclohexylamine (1 ml., 8.7 mmole) is added to a cold (0°) solution of 1-[[[(S)-3-[[(4-nitrophenoxy)carbonyl]amino]-2-oxo-4-phenylbutyl]methylamino]carbonyl]-L-proline, phenylmethyl ester (0.9 g., 1.58 mmole) in toluene in one portion. The solution turns yellow immediately and TLC indicates all starting material has been consumed. The resulting solution is washed sequentially with water, 1N hydrochloric acid, and 10% sodium bicarbonate. The organic layer is dried (MgSO4) and concentrated to a pale yellow oil. The crude product is purified (2×) by preparative layer chromatography using ethyl acetate as eluant to give 0.31 g. of 1-[[[(S)-3-[[(cyclohexylamino)carbonyl]amino]-2-oxo-4-phenylbutyl]methylamino]carbonyl]-L-proline, phenylmethyl ester as a clear, colorless salt.

(b)

1-[[[(S)-3-[[(Cyclohexylamino)carbonyl]amino]-2-oxo-4-phenylbutyl]methylamino]carbonyl]-L-proline A suspension of the phenylmethyl ester from part (a) (0.31 g., 0.56 mmole) in methanol and palladium hydroxide on carbon is hydrogenated at room temperature and atmospheric pressure for 30 minutes. The resulting mixture is filtered (Celite), the solids washed with methanol, and the filtrate concentrated to give 0.27 g. of a clear glass. The residue is triturated with ether and dried under vacuum to give 0.175 g. of 1-[[[(S)-3-[[(cyclohexylamino)carbonyl]amino]-2-oxo-4-phenylbutyl]methylamino]carbonyl]-L-proline; m.p. 75°–110°; $[\alpha]_D = 27°$ (c=1, methanol). TLC (silica gel; toluene:acetic acid, 4:1) $R_f = 0.18$.

Anal. calc'd. for $C_{24}H_{34}N_4O_5 \cdot 0.8H_2O$: C, 60.93; H, 7.59; N, 11.84. Found: C, 60.93; H, 7.40; N, 11.89.

EXAMPLE 4

1-[[Methyl[(S)-3-[[(4-methyl-1-piperazinyl)carbonyl]amino]-2-oxo-4-phenylbutyl]amino]carbonyl]-L-proline, dihydrochloride (a)

1-[[Methyl[(S)-3-[[(4-methyl-1-piperazinyl)carbonyl]amino]-2-oxo-4-phenylbutyl]amino]carbonyl]-L-proline, phenylmethyl ester N-Methyl piperazine (1 ml., 9.0 mmole) is added to a cooled (0°) solution of 1-[[[(S)-3-[[(4-nitrophenoxy)carbonyl]amino]-2-oxo-4-phenylbutyl]methylamino]carbonyl]-L-proline, phenylmethyl ester (1.06 g., 1.8 mmole) in toluene (20 ml.) in an ice bath in one portion. The resulting solution is stirred for an additional 45 minutes as it warms to room temperature. The solution is washed sequentially with water and 10% sodium bicarbonate, dried (MgSO4), and concentrated. The crude product is chromatographed on LPS-1 silica gel eluting with a solution of ethyl acetate:pyridine:acetic acid:water (300:20:6:11→100:20:6:11). Fractions containing the desired product are combined and concentrated to give 0.3 g. of 1-[[methyl[(S)-3-[[(4-methyl-1-piperazinyl)carbonyl]amino]-2-oxo-4-phenylbutyl]amino]carbonyl]-L-proline, phenylmethyl ester; TLC (silica gel; ethyl acetate:pyridine:acetic acid:water, 100:20:6:11) $R_f = 0.26$.

(b)

1-[[Methyl[(S)-3-[[(4-methyl-1-piperazinyl)carbonyl]amino]-2-oxo-4-phenylbutyl]amino]carbonyl]-L-proline, dihydrochloride A solution of the phenylmethyl ester product from part (a) (0.3 g., 0.54 mmole) in methanol (20 ml.) is hydrogenated for one hour at room temperature and atmospheric pressure using palladium hydroxide as catalyst. The resulting mixture is filtered and concentrated to a yellow oil. The crude product is dissolved in water and washed with ether, ethyl acetate, and chloroform. The aqueous layer is treated with 1N hydrochloric acid (0.5 ml.) and chromatographed on HP-20 using a 0.01N hydrochloric acid:methanol (100→0%) gradient. Fractions containing the desired product are combined, concentrated and lyophilized to give 0.042 g. of 1-[[methyl[(S)-3-[[(4-methyl-1-piperazinyl)carbonyl]amino]-2-oxo-4-phenylbutyl]amino]carbonyl]-L-proline, dihydrochloride as a bright yellow solid; m.p. (95) 101°–106°; $[\alpha]_D = -16°$ (c=0.4, methanol).

TLC (silica gel; n-butanol:acetic acid:water:ethyl acetate, 1:1:1:1) $R_f = 0.37$.

Anal. calc'd. for $C_{23}H_{33}N_5O_5 \cdot 2HCl \cdot 1.7H_2O$: C, 49.06; H, 6.87; N, 12.44; Cl, 12.59. Found: C, 49.02; H, 7.08; N, 12.29; Cl, 12.37.

EXAMPLE 5

1-[[[(S)-3-[[(Dimethylamino)carbonyl]amino]-2-oxo-4-phenylbutyl]methylamino]carbonyl]-L-proline (a)

1-[[[(S)-3-[[(Dimethylamino)carbonyl]amino]-2-oxo-4-phenylbutyl]methylamino]carbonyl]-L-proline, phenylmethyl ester Diisopropylethylamine (1.5 ml., 8.75 mmole) is added to a cooled (0°) solution of 1-[[[(S)-3-[[(4-nitrophenoxy)carbonyl]amino]-2-oxo-4-phenylbutyl]methylamino]carbonyl]-L-proline, phenylmethyl ester (1.0 g., 1.75 mmole) and dimethylamine hydrochloride (0.71 g., 8.75 mmoles) in toluene (50 ml.) in one portion. The resulting yellow solution is stirred in a closed system at 0° for 4 hours and for 2 hours following removal of the ice bath. The resulting mixture is washed sequentially with water, 10% sodium bicarbonate, 1N hydrochloric acid, and 10% sodium bicarbonate. The solution is dried (MgSO4) and concentrated to a pale yellow oil which is chromatographed on LPS-1 silica gel using 50→100% ethyl acetate in hexane as eluant. Fractions containing the desired product are combined and concentrated to give 0.68 g. of 1-[[[(S)-3-[[(dimethylamino)carbonyl]amino]-2-oxo-4-phenylbutyl]methylamino]carbonyl]-L-proline, phenylmethyl ester as a clear oil. TLC (silica gel, ethyl acetate) $R_f = 0.2$.

(b)

1-[[[(S)-3-[[(Dimethylamino)carbonyl]amino]-2-oxo-4-phenylbutyl]methylamino]carbonyl]-L-proline A solution of the phenylmethyl ester product from part (a) (0.68 g., 1.37 mmole) in methanol is hydrogenated at room temperature and atmospheric pressure for three hours using palladium hydroxide on carbon as catalyst. The resulting solution is filtered and concentrated to a white foam which is lyophilized from dioxane/water to give 0.5 g. of 1-[[[(S)-3-[[(dimethylamino)-carbonyl]amino]-2-oxo-4-phenylbutyl]methylamino]-carbonyl]-L-proline; m.p. (60) 74°-104°; $[\alpha]_D = -38.6°$ (c=1.0, methanol). TLC (silica gel; chloroform:methanol:acetic acid, 4:1:1) $R_f=0.73$, trace at 0.33.

Anal. calc'd. for $C_{22}H_{28}N_4O_5 \cdot 1.1H_2O$: C, 56.62; H, 7.17; N, 13.20. Found: C, 56.63; H, 7.25; N, 13.14.

EXAMPLES 6-30

Following the procedure of Examples 1-5, the amine shown in Col. I is treated with 4-nitrophenyl chloroformate and then reacted with the amine shown in Col. II to yield the ester product shown in Col. III. Removal of the $R_6$ ester group yields the corresponding acid product.

Col. I

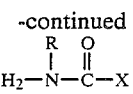

Col. II

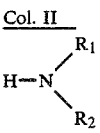

Col. III

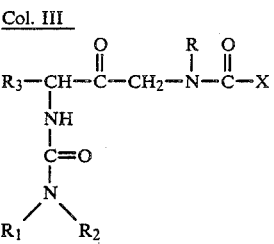

| Example | R₃ | $-N\begin{smallmatrix}R_1\\R_2\end{smallmatrix}$ | R | X |
|---|---|---|---|---|
| 6 | benzyl (PhCH₂–) | –NH₂ | –CH₃ | –N–CH₂–CH(CH₃)–CH₂–CH(COOCH₂Ph)(H) (L) |
| 7 | benzyl (PhCH₂–) | –NH–CH₃ | –CH₃ | –N–CH₂–CH(OPh)–CH₂–CH(COOCH₂Ph)(H) (L) |
| 8 | phenyl | –N(C₂H₅)₂ | –CH₃ | –N–CH₂–CH(cyclohexyl)–CH₂–CH(COOCH₂Ph)(H) (L) |
| 9 | 2-pyridylmethyl | –NH–CH₂–Ph | –CH₃ | –N–CH₂–CH(Ph)–CH₂–CH(COOCH₂Ph)(H) (L) |

-continued
| Example | R₃ | $\begin{matrix} R_1 \\ -N \\ R_2 \end{matrix}$ | R | X |
|---|---|---|---|---|
| 10 |  | 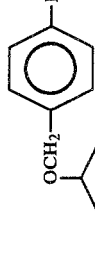 | —CH₃ |  |
| 11 |  |  | —CH₃ |  |
| 12 | 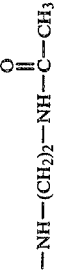 |  | —CH₃ |  |
| 13 |  |  | —CH₃ |  |
| 14 | H₅C₂—H₂C— |  | —CH₃ |  |

-continued

| Example | R₃ | R | NR₁R₂ | X |
|---|---|---|---|---|
| 15 | cyclohexyl-CH₂— | —NH—(CH₂)₃—NH—C(O)—OCH₂—C₆H₅ | —CH₃ | 2-benzyl-phenyl fused to N, with —COOCH₂C₆H₅, H (L) |
| 16 | C₆H₅—CH₂— | —NH—(CH₂)₄—O—CH₂—C₆H₅ | —CH₃ | 2-(CH₂-)phenyl fused to N, with —COOC(CH₃)₃, H (L) |
| 17 | C₆H₅—CH₂—O—C(O)—HN—(CH₂)₄— | pyrrolidin-1-yl (—N⟨ ⟩) | —CH₃ | 2-substituted cyclohexyl to N, with —COOCH₂C₆H₅, H (L) |
| 18 | C₆H₅—CH₂— | azepan-1-yl (—N⟨ ⟩) | —CH₃ | 2-(CH₂-)cyclohexyl fused to N, with —COOCH₂C₆H₅, H (L) |
| 19 | C₆H₅—CH₂— | 4-(C₆H₅—CH₂—O—C(O)—)piperazin-1-yl | —CH₂—C₆H₅ | —N—CH₂—S—CH₂—CH(COOC(CH₃)₃)(H) (L) |

-continued

| Example | R₃ | NR₁R₂ | R | X |
|---|---|---|---|---|
| 20 | benzyl | 4-methylpiperidin-1-yl | -CH₂-(2-indolyl)(NH) | -N(cyclopentyl-fused)-CH(COOCH₂Ph)(H) (L) |
| 21 | benzyl | piperidin-1-yl | -(CH₂)₄-NH-C(=O)-O-CH₂-Ph | -N(cyclohexyl)-CH(COOCH₂Ph)(H) (L) |
| 22 | benzyl | 3-methoxypiperidin-1-yl | -(CH₂)₂-O-CH₂-Ph | -N(Ph)-CH₂-COOC(CH₃)₃ |
| 23 | benzyl | 3-chloropyrrolidin-1-yl | -CH₃ | -N(cyclohexyl)-CH₂-COOCH₂Ph |
| 24 | (2-pyridyl)methyl | 4-methyl-azepan-1-yl | -CH₃ | -NH-CH(CH₃)-COOCH₂Ph (L) |
| 25 | benzyl | morpholin-4-yl | -CH₃ | -NH-CH(CH₂-CH(CH₃)₂)-COOCH₂Ph (L) |

-continued

| Example | R₃ | R | X |
|---|---|---|---|
| 26 | C₆H₅CH₂— | —N(CH₃)₂ | —CH₃ | —NH—CH(L)(CH₂C₆H₅)—COOCH₂C₆H₅ |
| 27 | C₆H₅CH₂— | cyclohexyl-NH— | —CH₃ | —NH—CH(L)(CH₂—C(=N—N=CH—C₆H₅))—COOCH₂C₆H₅ |
| 28 | C₆H₅CH₂— | 4-methylpiperazin-1-yl | —CH₃ | N-substituted structure with COOCHOC(O)—C₂H₅ and cyclohexyl (L), phenylthio |
| 29 | 2-pyridyl-CH₂— | 4-ethylpiperazin-1-yl | —CH₃ | N-substituted structure with COOCHOC(O)—C₂H₅ and CH(CH₃)₂ (L) |

-continued

| Example | R₃ | R | X |
|---|---|---|---|
| 30 | C₆H₅-CH₂-, -N(R₁)(R₂) = morpholino | -CH₃ | -N(H)-CH₂-CH(C₆H₁₁)-CH₂-C(O)O-CH(CH(CH₃)₂)-O-C(O)-O-C₂H₅ |

The R₃ protecting group shown in Example 17, the R₁ protecting groups shown in Examples 15 and 16, the R protecting groups shown in Examples 21 and 22, the R₅ protecting group shown in Example 27, and the R₂₆ protecting group shown in Example 19 are removed as the last step in the synthesis. The R₆ ester groups shown in Examples 28 to 30 are not removed.

EXAMPLE 31

1000 tablets each containing the following ingredients:

| | |
|---|---|
| 1-[[Methyl[(S)—2-oxo-4-phenyl-3-[(1-piperidinylcarbonyl)amino]-butyl]amino]carbonyl]-L-proline | 100 mg. |
| Cornstarch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the 1-[[methyl[(S)-2-oxo-4-phenyl-3-[(1-piperidinylcarbonyl)amino]butyl]amino]carbonyl]-L-proline and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 30 can be prepared.

A similar procedure can be employed to form tablets containing 50 mg. of active ingredient.

EXAMPLE 32

Two piece #1 gelatin capsules are filled with a mixture of the following ingredients:

| | |
|---|---|
| 1-[[Methyl[(S)—3-[(4-morpholinyl-carbonyl)amino]-2-oxo-4-phenyl-butyl]amino]carbonyl]-L-proline | 50 mg. |
| Magnesium stearate | 7 mg. |
| Lactose | 193 mg. |
| | 250 mg. |

In a similar manner capsules containing 50 mg. of the product of any of Examples 1 and 3 to 30 can be prepared.

EXAMPLE 33

An injectable solution is prepared as follows:

| | |
|---|---|
| 1-[[[(S)—3-[[(Cyclohexylamino)-carbonyl]amino]-2-oxo-4-phenyl-butyl]methylamino]carbonyl]-L-proline | 500 g. |
| Methyl paraben | 5 g. |
| Propyl paraben | 1 g. |
| Sodium chloride | 25 g. |
| Water for injection | 5 l. |

The active substance, preservatives and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1, 2 and 4 to 30.

EXAMPLE 34

1000 tablets containing the following ingredients:

| | |
|---|---|
| 1-[[[(S)—3-[[(Dimethylamino)-carbonyl]amino]-2-oxo-4-phenyl-butyl]methylamino]carbonyl]-L-proline | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 250 mg. | are prepared from sufficient bulk quantities by slugging the 1-[[[(S)-3-[[(dimethylamino)carbonyl]amino]-2-oxo-4-phenylbutyl]methylamino]carbonyl]-L-proline, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In similar manner, tablets can be prepared containing 100 mg. of the product of any of Examples 1 to 4 and 6 to 30.

What is claimed is:

1. A compound of the formula $$R_3-CH-\underset{NH}{\overset{O}{\overset{\|}{C}}}-CH_2-\underset{}{\overset{R}{\overset{|}{N}}}-\overset{O}{\overset{\|}{C}}-X$$
$$\underset{R_1}{\overset{|}{\underset{}{N}}}\underset{R_2}{}$$
with NH—C=O attached including a pharmaceutically acceptable salt thereof wherein:

X is $$\underset{H}{\overset{R_7}{\underset{|}{-N-\underset{|}{\overset{H_2C}{\diagup}\overset{CH_2}{\diagdown}}-C-COOR_6,}}}\ (L)$$

$$\underset{H}{\overset{}{\underset{|}{-N-\underset{|}{\overset{H_2C}{\diagup}\overset{CH_2}{\diagdown}\overset{R_8}{-}}-C-COOR_6,}}}\ (L)$$

$$\underset{H}{\overset{R_9}{\underset{|}{-N-\underset{|}{\overset{}{\diagup}\overset{CH_2}{\diagdown}\overset{CH_2}{}}-C-COOR_6,}}}\ (L)$$

$$\underset{H}{\overset{R_{10}\diagdown\diagup R_{10}}{\underset{|}{-N-\underset{|}{\overset{H_2C}{\diagup}\overset{CH_2}{\diagdown}}-C-COOR_6,}}}\text{ or }\ (L)$$

$$-N\overset{\frown}{\underset{H}{\underset{|}{-}}}C-COOR_6;\ (L)$$

$R_7$ is hydrogen, lower alkyl, halogen, hydroxy,
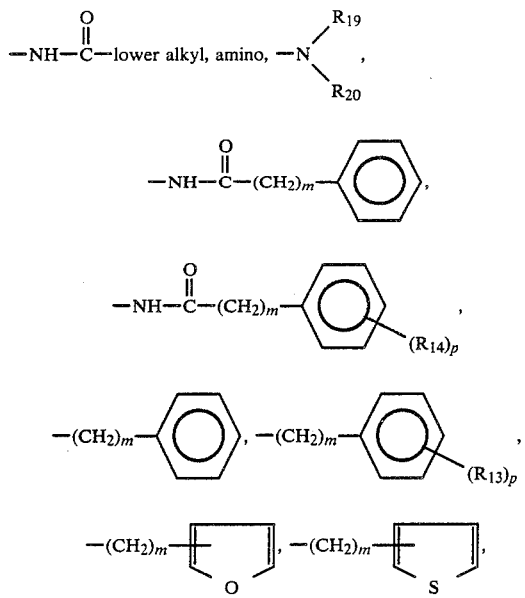
a 1- or 2-naphthyl of the formula
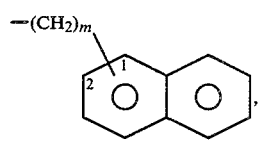
a substituted 1- or 2-naphthyl of the formula
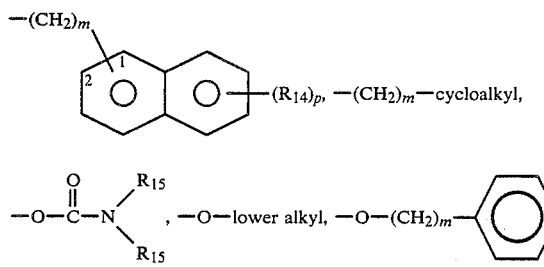
a 1- or 2-naphthyloxy of the formula
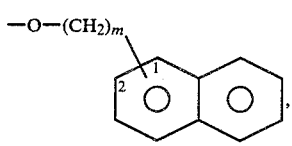
a substituted 1- or 2-naphthyloxy of the formula
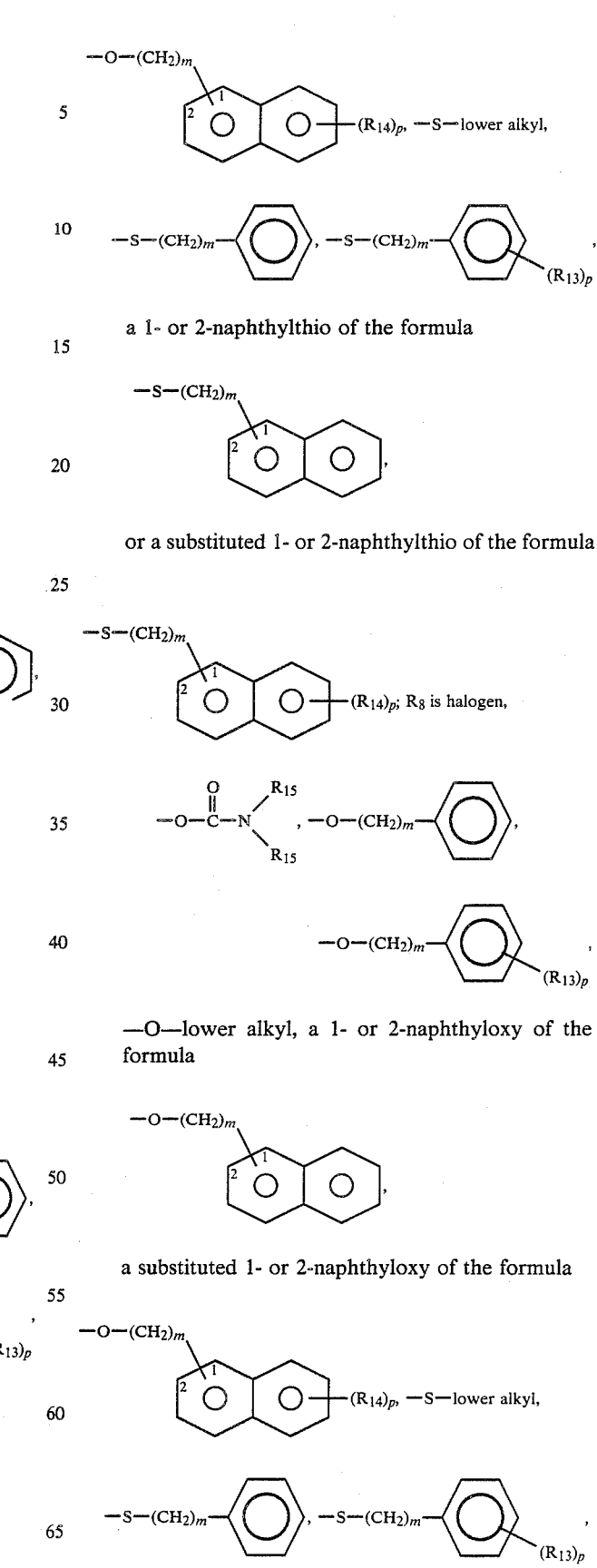
—O—lower alkyl, a 1- or 2-naphthyloxy of the formula
a substituted 1- or 2-naphthyloxy of the formula
a 1- or 2-naphthylthio of the formula or a substituted 1- or 2-naphthylthio of the formula $R_9$ is keto, $R_{10}$ is halogen or $-Y-R_{16}$;
$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy;
m is zero, one, two, three, or four;
p is one, two or three provided that p is more than one only if $R_{13}$ or $R_{14}$ is methyl, methoxy, chloro, or fluoro;
$R_{15}$ is hydrogen or lower alkyl of 1 to 4 carbons;
Y is oxygen or sulfur;
$R_{16}$ is lower alkyl of 1 to 4 carbons, r is an integer from 1 to 4;
$R_{19}$ is lower alkyl, benzyl or phenethyl;
$R_{20}$ is hydrogen, lower alkyl, benzyl or phenethyl;
R is hydrogen, lower alkyl, halo substituted lower alkyl, $R_1$ and $R_2$ taken together with the N atom to which they are attached complete a heterocyclic ring of the formula v is an integer from 2 to 6;
$R_{26}$ is hydrogen or lower alkyl;
n is zero, one, or two;
$R_3$ is hydrogen, lower alkyl, , halo substituted lower alkyl, $$-(CH_2)_r-\underset{\underset{H}{|}}{\overset{N}{\diagdown}}N, \quad -(CH_2)_r-NH_2, \quad -(CH_2)_r-SH,$$

$$-(CH_2)_r-S-\text{lower alkyl}, \quad -(CH_2)_r-NH-\underset{NH_2}{\overset{NH}{\diagup}}C, \text{ or }$$

$$-(CH_2)_r-\overset{O}{\underset{\|}{C}}-NH_2;$$

$R_6$ is hydrogen, lower alkyl, benzyl, benzhydryl, $$-\underset{R_{17}}{\overset{|}{CH}}-O-\overset{O}{\underset{\|}{C}}-R_{18}, \quad -\underset{R_{22}}{\overset{R_{21}}{\underset{|}{C}}}-\overset{O}{\underset{\|}{C}}-O-R_{23}, \quad -CH-(CH_2-OH)_2,$$

$$-CH_2-\underset{OH}{\overset{|}{CH}}-\underset{OH}{\overset{|}{CH}_2}, \quad -(CH_2)_2-N(CH_3)_2, \text{ or } -(CH_2)_r-\langle\text{pyridinyl}\rangle;$$

$R_{17}$ is hydrogen, lower alkyl, cycloalkyl, or phenyl;
$R_{18}$ is hydrogen, lower alkyl, lower alkoxy or phenyl;
$R_{21}$ and $R_{22}$ are independently selected from the group consisting of hydrogen and lower alkyl; and
$R_{23}$ is lower alkyl.

2. A compound of claim 1 wherein:
X is $$\underset{H_2C}{\overset{R_7}{\underset{|}{CH}}}\underset{CH_2}{\overset{}{}}$$
$$-N\underset{H}{\overset{}{-}}\underset{(L)}{\overset{}{C}}-COOR_6;$$

$R_6$ is hydrogen or an alkali metal salt ion;
$R_7$ is hydrogen, cyclohexyl, lower alkoxy of 1 to 4 carbons, $$-(CH_2)_m-\langle\text{phenyl}\rangle, \quad -(CH_2)_m-\langle\text{phenyl}\rangle_{R_{13}},$$

$$-O-(CH_2)_m-\langle\text{phenyl}\rangle, \quad -O-(CH_2)_m-\langle\text{phenyl}\rangle_{R_{13}},$$

$$-S-(CH_2)_m-\langle\text{phenyl}\rangle \text{ or } -S-(CH_2)_m-\langle\text{phenyl}\rangle_{R_{13}};$$

m is zero, one or two; and
$R_{13}$ is methyl, methoxy, methylthio, chloro, bromo, fluoro, or hydroxy.

3. A compound of claim 2 wherein:

R is straight or branched chain lower alkyl of 1 to 4 carbons;
$R_1$ and $R_2$ taken together with the N atom to which they are attached complete a heterocyclo ring of the formula $$-N\langle\text{piperidinyl}\rangle, \quad -N\langle\text{piperidinyl}\rangle_{R_{14}}, \text{ or } -N\langle\text{piperazinyl}\rangle N-R_{26};$$

$R_{26}$ is hydrogen or straight or branched chain lower alkyl of 1 to 4 carbons;
$R_3$ is straight or branched chain lower alkyl of 1 to 4 carbons, $$-(CH_2)_m-\langle\text{phenyl}\rangle, \text{ or } -(CH_2)_m-\langle\text{phenyl}\rangle_{R_{14}};$$

m is zero, one, or two; and
$R_{14}$ is methyl, methoxy, methylthio, Cl, Br, F, or hydroxy.

4. A compound of claim 3 wherein:
X is $$-N\underset{H}{\overset{}{-}}\underset{(L)}{\overset{}{C}}-COOR_6;$$

R is methyl; and
$R_6$ is hydrogen or an alkali metal salt ion.

5. A compound of claim 4 wherein $R_1$ and $R_2$ taken together with the N atom to which they are attached complete a heterocyclo ring of the formula $$-N\langle\text{piperidinyl}\rangle, \text{ or } -N\langle\text{piperazinyl}\rangle N-CH_3.$$

6. The compound of claim 5, 1-[[methyl[(S)-2-oxo-4-phenyl-3-[(1-piperidinylcarbonyl)amino]butyl]amino]-carbonyl]-L-proline.

7. The compound of claim 5, 1-[[methyl[(S)-3-[[(4-methyl-1-piperazinyl)carbonyl]amino]-2-oxo-4-phenyl-butyl]amino]carbonyl]-L-proline, dihydrochloride salt.

8. A pharmaceutical composition useful for treating hypertension comprising a pharmaceutically acceptable carrier and a hypotensive compound of the formula $$R_3-\underset{\underset{\underset{\underset{R_1}{\overset{|}{N}}\diagdown R_2}{\overset{|}{N}}}{\overset{|}{C=O}}}{\overset{|}{NH}}}\overset{O}{\underset{\|}{C}}-CH_2-\underset{\overset{|}{R}}{\overset{|}{N}}-\overset{O}{\underset{\|}{C}}-X$$

wherein R, $R_1$, $R_2$, $R_3$ and X are as defined in claim 1.

* * * * *